(12) United States Patent
Baldet

(10) Patent No.: US 12,114,627 B2
(45) Date of Patent: Oct. 15, 2024

(54) AIR-MOVING DEVICE EMPLOYING COANDA EFFECT FOR POLLINATING A RECIPIENT PLANT USING POLLEN COLLECTED FROM A DONOR PLANT

(71) Applicants: Institut national de recherche pour l'agriculture, l'alimentation et l'environnement, Paris (FR); ASUR PLANT BREEDING, Estrées-Saint-Denis (FR); SYNGENTA FRANCE SAS, Saint-Sauveur (FR)

(72) Inventor: Patrick Baldet, Pressigny les Pins (FR)

(73) Assignees: Institut national de recherche pour l'agriculture, l'alimentation et l'environnement, Paris (FR); ASUR PLANT BREEDING, Estrées-Saint-Denis (FR)

( * ) Notice: Subject to any disclaimer, the term of this patent is extended or adjusted under 35 U.S.C. 154(b) by 896 days.

(21) Appl. No.: 16/978,112

(22) PCT Filed: Mar. 14, 2019

(86) PCT No.: PCT/FR2019/050562
§ 371 (c)(1),
(2) Date: Sep. 3, 2020

(87) PCT Pub. No.: WO2019/175507
PCT Pub. Date: Sep. 19, 2019

(65) Prior Publication Data
US 2021/0045306 A1      Feb. 18, 2021

(30) Foreign Application Priority Data
Mar. 14, 2018   (FR) .................................... 18 52209

(51) Int. Cl.
*A01H 1/02*        (2006.01)
*A01B 59/06*       (2006.01)

(52) U.S. Cl.
CPC ........... *A01H 1/027* (2021.01); *A01B 59/064* (2013.01)

(58) Field of Classification Search
CPC .................................................... A01H 1/027
See application file for complete search history.

(56) References Cited

U.S. PATENT DOCUMENTS 4,087,937 A * 5/1978 Meader .................. A01H 1/027
                                                       47/1.41
2014/0245843 A1   9/2014 Bry
                         (Continued)

FOREIGN PATENT DOCUMENTS

FR         2866784            9/2005
FR         2866784 A1 *       9/2005    ............... A01H 1/02
                         (Continued)

OTHER PUBLICATIONS

International Search Report dated May 23, 2019.

*Primary Examiner* — Kristen C Hayes
(74) *Attorney, Agent, or Firm* — IPSILON USA, LLP

(57) ABSTRACT

An air-moving device (10) for pollinating at least one recipient plant using pollen collected on at least one donor plant includes a pollen collector for collecting pollen from the at least one said donor plant, and a distributor for distributing pollen on at least one recipient plant. A channel for conveying the pollen collected from the pollen collector to the distributor is provided. An air flow amplifier (18) employs Coanda effect for inducing a flow of air inside the conveying channel (16) from the pollen collector to the distributor for distributing the pollen. A pneumatic deflector
(Continued)

deflects the Coanda effect flow of pollen disposed at the level of the pollen distributor.

16 Claims, 5 Drawing Sheets

(56) References Cited

U.S. PATENT DOCUMENTS

| | | | | |
|---|---|---|---|---|
| 2018/0310468 | A1* | 11/2018 | Schoeny | A01C 7/102 |
| 2021/0337736 | A1* | 11/2021 | Boyer | B01D 45/16 |

FOREIGN PATENT DOCUMENTS

| | | | | |
|---|---|---|---|---|
| FR | 2979798 | | 3/2013 | |
| FR | 2979798 | A1 * | 3/2013 | A01H 1/025 |
| GB | 2542507 | | 3/2017 | |
| GB | 2542507 | A * | 3/2017 | A47L 5/16 |
| KR | 20130073168 | | 7/2013 | |
| WO | WO-2013050066 | A1 * | 4/2013 | G01N 1/2211 |
| WO | WO-2016085355 | A1 * | 6/2016 | A01H 1/025 |

* cited by examiner

AIR-MOVING DEVICE EMPLOYING COANDA EFFECT FOR POLLINATING A RECIPIENT PLANT USING POLLEN COLLECTED FROM A DONOR PLANT

RELATED APPLICATION

This application is a National Phase of PCT/FR2019/050652 filed on Mar. 14, 2019 which claims the benefit of priority from French Patent Application No. 18 52209, filed on Mar. 14, 2018, the entirety of which are incorporated by reference.

FIELD OF THE INVENTION

The present invention concerns an air-moving device for pollinating a recipient plant using pollen collected from a donor plant. The invention concerns in particular a device comprising a Coanda effect air flow amplifier, also known as an "air amplifier" or "air mover". The invention also concerns a pneumatic deflector for deflecting the Coanda effect flow of pollen disposed at the level of the pollen distributing means.

The invention also concerns an apparatus and a vehicle comprising this kind of air-moving device.

DESCRIPTION OF RELATED ART

In the field of reproduction of plants, a plant is pollinated by transferring male gametes (pollen) to the female recipient members (stigmata) of a plant. This transfer may be effected by wind, in which case the plants are referred to as anemophile pollination plants.

For some crops, natural pollination may prove impossible or more generally insufficient under natural conditions therefore leading to recourse to assisted artificial pollination. This assisted artificial pollination can take two forms:

the exclusive artificial pollination process in which the only source of pollen is exogenous and applied by an artificial means to a plant having no natural source of pollen; for example, this is the case of single-sex dioecious species that must therefore receive exogenous pollen;

the pollen supplementation process in which natural pollination is reinforced by adding pollen that may come from an exogenous source or from the pollinated plant itself.

Anemophile pollination plants belong to two very distinct groups: plants having "orthodox" pollen and plants having "recalcitrant" pollen. The terms "orthodox" and "recalcitrant" are derived from the names of seeds classed as a function of their tolerance to drying out and storability. Seeds are termed "orthodox" when they have good tolerance to drying out and good storability. In contrast, seeds for which drying out is lethal are termed "recalcitrant".

So-called "orthodox" pollen has the capability of drying out before being released by the male members (anthers) and carried off by wind. This pollen has the capability of becoming dormant and have reserves. It therefore has extended viability enabling it to fly far away from the pollinating plant whilst conserving its reproduction potential. The pollen is rehydrated and becomes capable of reproduction on arriving on the collecting apparatus of the female flower. This type of pollen withstands drying out and its mass is low and predisposes it to be carried easily by wind. This relatively robust type of pollen therefore lends itself easily to large-scale storage and artificial pollination such as in the case of Kiwi (*Actinidia chinensis,* Planch.) pollen for the production of fruit or in the case of the pollen of conifer trees.

So-called "recalcitrant" pollen is intended for virtually immediate pollination because its viability is very short-lived and conditional upon maintaining a high level of hydration. This is the case of the pollen of wheat (*triticum* sp.), barley (*hordeum* sp.), rice (*oryza* sp.) or maize (*Zea mays* sp.). These pollens cannot be stored easily, are very fragile and require many precautions in handling them. Artificial pollination of plants having this kind of pollen involves specific technologies and practices respecting the very ephemeral viability of these pollens. The viability of the pollen corresponds to its reproduction potential.

There is known from the document FR 2 866 784 A1 an apparatus for collecting pollen from plants, including maize and for distributing it to the female members of other plants. That apparatus comprises a Venturi effect system for generating a flow of air that both aspirates the pollen and transports it to the points of application. This Venturi effect system for generating a flow of air comprises a nozzle for injecting drive air under pressure into the transport pipe to generate a flow of air in that pipe by the Venturi effect. This injection nozzle partly clutters the pipe for aspirating the pollen and constitutes a major source of friction and impacts harmful to fragile pollen such as those of cereals. Moreover, this primary air is introduced into the aspiration pipe under turbulent conditions, which compromises the viability of the pollen. In particular, the injection of drive air by the nozzle generates a central zone of high turbulence, of centrifugal expansion of the drive air under pressure, and of excess speeds also compromising fragile pollen, i.e. "recalcitrant" pollen. Moreover, the presence of bifurcations or changes of direction, or bends, during transportation of the pollen favors the agglomeration and settling of the grains of pollen which also compromises their viability.

In the same document FR 2 866 784 A1 the Venturi effect system for generating a flow of air may also comprise a turbine, which implies the presence of a mechanical fan in the pipe and therefore impacts and high accelerations of the pollen passing through it. Moreover, mechanical fans very often generate centrifugal forces that also contribute to throwing the aspirated particles against the walls. These two solutions for generating the flow of air transporting the pollen are therefore unable to guarantee the viability of the transported pollen, or reduce it very markedly, when the latter is of the "recalcitrant" type.

Moreover, the aspiration pipe of this collecting apparatus is divided into a plurality of ducts for distributing the pollen. These bifurcations also constitute a multitude of obstacles compromising the viability of "recalcitrant" pollen.

The document KR 10-1390504 also describes an apparatus for collecting and then distributing pollen. That apparatus also comprises a Venturi effect system for generating a flow of air to create an aspiration and blowing flow of air. This system for generating the flow of air for transporting the pollen includes an annular pipe for injecting drive air formed by two concentric duct portions inside the pollen aspiration and transport pipe. The duct portion having the smaller diameter is formed by the aspiration pipe itself, thereby inducing a sudden and large reduction of section. This configuration is very unfavorable for the viability of the pollen when the latter is of the "recalcitrant" type.

Also, the passage section formed by the annular drive air injection pipe is much greater than that of the aspiration pipe at the level of the Venturi system and therefore cannot provide a function of amplifying the ratio of the drive air to the induced flow of air. This passage section ratio results in the injected drive air forming a very large portion of the flow of air generated inside the aspiration pipe relative to the air induced by the injection of the drive air. On the basis of the ratio of the tube sections shown and the expansion of the drive air it is possible to estimate that the total blowing air drive air flow consists of only 10% of the flow of air generated in the aspiration pipe, as against 90% drive air. Consequently, in this system the aspiration flow remains at a low flow rate whereas the total blowing flow is to the contrary increased tenfold. The transport of fragile and greatly hydrated pollen requires on the other hand a speed reduction that in particular imposes the greatest possible equivalency between the speed of aspiration of the pollen imposed by the natural rate of sedimentation of said pollen and the blowing speed which must not be significantly accelerated without risking causing impacts and friction of a kind that reduces the viability of the pollen.

There moreover exist portable devices employing air flow amplification for aspirating pollen (or other particles) and storing it after separation of the aspiration flow of air and the blowing flow of air. These portable devices may comprise a cyclone for separation by gravity. It has been demonstrated that the passage of fragile or recalcitrant pollen in this kind of gravimetric separation cyclone is lethal for that pollen even if the gravimetric separation has been the subject of a reduction of friction forces and other mechanical impacts inflicted on the pollen (cf. the publication Irstea/Cemagref, 2008 “Reproduction sexuée des conifères et production de semences en vergers à graines, partie Technologie du Pollen, pp. 279 à 285, auteurs Gwenaël Philippe, Patrick Baldet, Bernard Héois & Christian Ginisty” [Sexual reproduction of conifers and production of seeds in seed orchards, pollen technology part, pp. 279 to 285, authors Gwenaël Philippe, Patrick Baldet, Bernard Héois & Christian Ginisty].

OBJECTS AND SUMMARY

There therefore exists a need for a device enabling pollination of a recipient plant using pollen collected from a donor plant, configured to guarantee the viability of the collected pollen until it is distributed if the latter is of the “recalcitrant” type.

To this end, the invention concerns an air-moving device for pollinating at least one recipient plant using pollen collected on at least one donor plant, comprising:

- a means for collecting pollen from said at least one donor plant,
- a means for distributing pollen on at least one recipient plant,
- a channel for conveying the pollen collected from the collecting means to the distributing means,
- an air flow amplifier which employs Coanda effect for inducing a flow of air inside the conveying channel from the means for collecting the pollen to the means for distributing the pollen.

The air flow amplifier enables an aspiration air stream to be induced in its upstream part and a blowing flow in its downstream part combining primary drive air injected under pressure into the conveying channel and the induced secondary flow of air. Thanks to a laminar, high-velocity flow of drive air, the Coanda effect enables maximum generation of a zone of reduced pressure and therefore inducing amplification of the blowing and induced aspiration flow. This technical solution also features a minimum of obstacles at the level of the passage section in which the air flow amplifier is disposed, in particular compared to a Venturi effect air flow generator. In fact, the aspiration and blowing flows may be induced without any significant reduction of the diameter of the conveying channel, as in the document KR 10-1390504, and without the presence of any localized obstacle inside that passage section, such as the air injection nozzle in the document FR 2 866 784 A1. The use of drive air injection nozzles cannot produce a laminar or mostly laminar flow of air that makes it possible to limit impacts and therefore to maintain the viability of the pollen, in particular in the case of recalcitrant pollen. In fact, the flow of air generated by the injection nozzles is injected in a partly turbulent centrifugal expansion form that induces risks of throwing the pollen onto the walls of the conveying system and is therefore lethal for recalcitrant pollen. The use of injection nozzles to generate the conveying flow of air is therefore a solution that is ill adapted to transporting this very fragile type of pollen.

Moreover, the use of a Coanda effect air flow amplifier enables a very high ratio to be obtained between the secondary flow of air in the conveying channel and the inducing compressed gas flow, in particular compared to a Venturi effect air flow generator. Thus the use of the Coanda effect enables very great amplification of the flow of air inside the conveying channel for a small input of primary drive air and consequently a small increase in the speed of the blowing flow of air relative to the aspiration flow of air.

Consequently, the Coanda effect air flow amplifier enables great amplification of the flow of air inside the conveying channel whilst limiting the elements that can form an obstacle for the pollen inside the conveying channel. As stated above, reducing these obstacles therefore enables total respect for the viability of the pollen transported when the latter is of the “recalcitrant” type.

In accordance with one embodiment of the air-moving device, the conveying channel is formed by a plurality of pipe elements, the Coanda effect air flow amplifier including:

- a pipe forming one of said pipe elements of the conveying channel,
- an orifice formed in the pipe,
- a source of compressed gas in fluid communication with the orifice to feed the conveying channel with compressed gas,
- an interior edge at least partly defining the orifice and forming a convex surface configured to generate a Coanda effect on a primary drive gas flow generated by the source of compressed gas via the orifice.

In accordance with one embodiment of the air-moving device, the conveying channel extends around a conveying axis, the orifice extending along an angular sector around the conveying axis.

In accordance with one embodiment of the air-moving device, the air flow amplifier is configured to induce on the basis of the supply of compressed gas to the conveying channel a secondary flow of air at a predetermined speed where the ratio between said secondary air flow in the conveying channel and the primary drive gas flow is greater than or equal to 10, preferably greater than or equal to 15, more preferably greater than or equal to 17.

In accordance with one embodiment of the air-moving device, the air flow amplifier is disposed at the level of the collecting means.

In accordance with one embodiment of the air-moving device, the latter comprises a plurality of Coanda effect air flow amplifiers disposed in series along the conveying channel to participate at least partly in inducing the secondary flow of air inside the conveying channel.

In accordance with one embodiment of the air-moving device, the conveying channel has a pollen passage section the variation of which between the collecting means and the distributing means is equal to or less than 30%, preferably equal to or less than 20%, more preferably equal to or less than 10%.

In accordance with one embodiment of the air-moving device, the conveying channel extends in a rectilinear manner over at least 70%, preferably over at least 80%, more preferably over at least 90% of its total length.

In accordance with one embodiment of the air-moving device, the conveying channel is formed by a pipe comprising at the maximum three elbow portions between the collecting means and the distributing means.

In accordance with one embodiment of the air-moving device, each of the collecting means and the distributing means is formed by a box comprising:
- an upper wall having an opening in fluid communication with the conveying channel,
- two lateral walls extending from the upper wall,
- a front opening enabling the donor plant or the recipient plant to enter the box.

In accordance with one embodiment of the air-moving device, the collecting means further comprises:
- a mobile back wall disposed opposite the front opening relative to the upper wall, and/or
- a shaking means for shaking a donor plant disposed inside the box.

In accordance with one embodiment of the air-moving device, the shaking means comprises at least two rods extending between the two lateral walls, said at least two rods being spaced from one another in a direction extending between the front opening and the back wall.

In accordance with one embodiment of the air-moving device, the latter further comprises one or more pneumatic Coanda effect pollen deflectors disposed at the level of the distributing means.

The invention also concerns an air-moving apparatus for pollinating at least one recipient plant using pollen collected from at least one donor plant, comprising at least two air-moving devices as described hereinabove disposed side by side so that the conveying channels of the air-moving devices extend in the same direction, one of the air-moving devices being offset relative to the other air-moving device in said direction.

The invention further concerns a vehicle comprising a coupling structure and at least one air moving device as described hereinabove or at least one apparatus as described hereinabove fixed to the coupling structure so that the front openings of the collecting means and the distributing means of the air-moving devices are oriented in the same direction of advance to receive donor plants or recipient plants during movement of the vehicle in that direction of advance.

The invention further concerns the use of an air-moving device as described hereinabove for a type of pollen having a predetermined settling rate, in which the Coanda effect air flow amplifier induces a flow of air inside the conveying channel at a speed greater than the predetermined settling rate of the selected pollen type.

In accordance with one embodiment of the use of the air-moving device, the speed of the flow of air induced inside the conveying channel is less than or equal to 10 m·s$^{-1}$, preferably less than or equal to 5 m·s$^{-1}$.

BRIEF DESCRIPTION OF THE DRAWINGS

Other features and advantages of the invention will become apparent on reading the following description of preferred embodiments of the invention given by way of example and with reference to the appended drawings.

DETAILED DESCRIPTION

Figure 1:
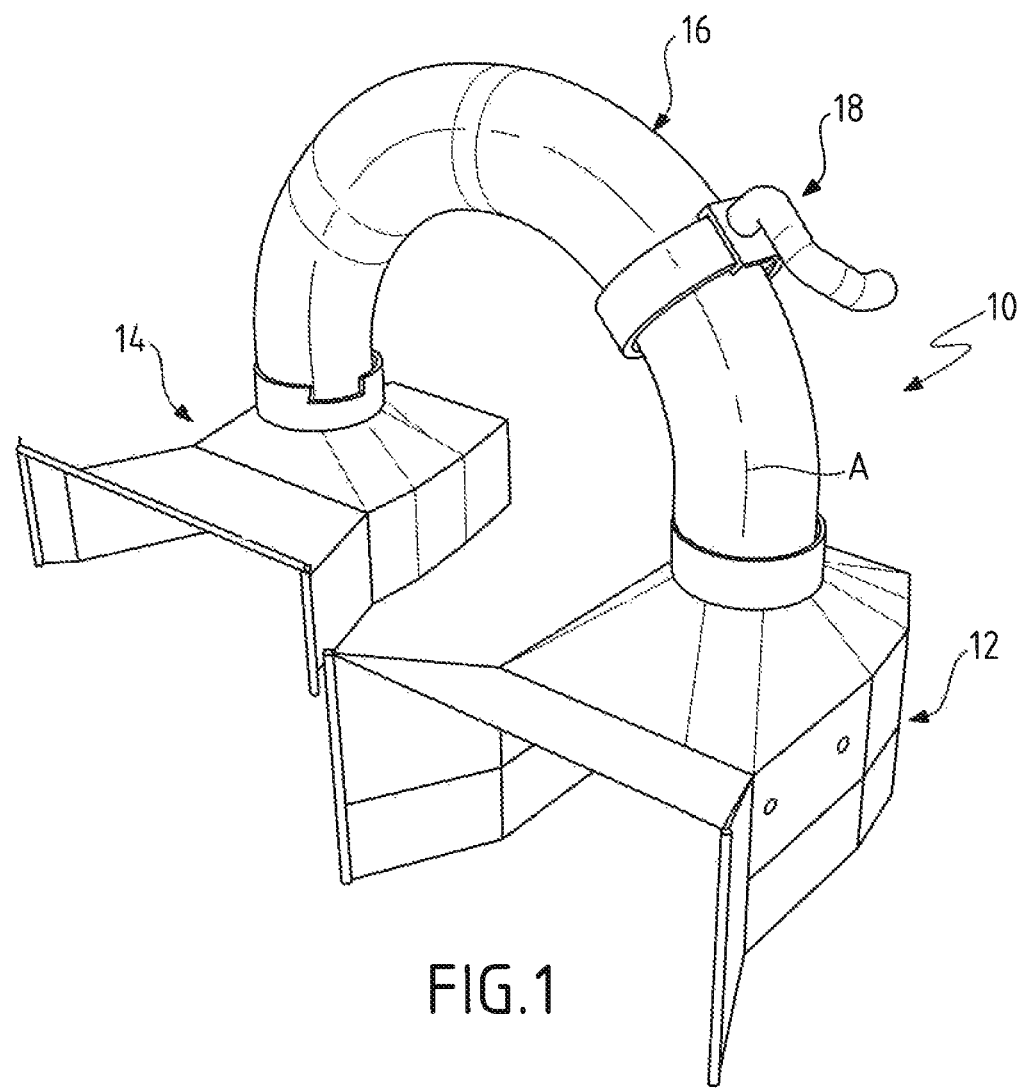
FIG. 1 represents a perspective view of one embodiment of an air-moving device.

An air-moving device 10 as represented in FIG. 1 is configured for pollination of at least one recipient plant using pollen collected from at least one donor plant. The collected pollen is preferably a "recalcitrant" type pollen such as a pollen of wheat (*triticum* sp.), barley (*hordeum* sp.), rice (*oryza* sp.) or maize (*Zea mays* sp.).

The air-moving device 10 comprises a means 12 for collecting pollen from said at least one donor plant. Here pollen designates interchangeably a grain of pollen or a plurality of grains of pollen. This collecting means 12 is configured to enable reception of a donor plant inside it during use of the air-moving device 10. This air-moving device 10 also comprises a means 14 for distributing the pollen collected from the donor plant onto at least one recipient plant. In a similar manner to the collecting means 12, the distributing means 14 is configured to enable reception of said at least one recipient plant inside it during use of the air-moving device 10. The air-moving device 10 further comprises a channel 16 for conveying the collected pollen from the collecting means 12 to the distributing means 14. This conveying channel 16 forms a duct extending from the collecting means 12 to the distributing means 14. To reduce the elements that may constitute an obstacle to the pollen, the conveying channel 16 is preferably formed by a duct of arch or elbow shape. In this case, the conveying channel 16 preferably includes a single elbow. Thus the conveying channel 16 features only one continuous change of direction from an upward vertical direction to a downward vertical direction. More generally, the conveying channel 16 is preferably formed by a duct comprising at the maximum three elbow portions, preferably at the maximum two elbow portions, between the collecting means 12 and the distributing means 14.

The use of a channel for conveying the pollen enables control of the trajectory of the pollen between the donor plant and the recipient plant and optimization of the speed and energy of the conveying air-moving flow. Thus it is possible to favor zones naturally deficient in pollen during use of the air-moving device 10. Such control is not possible, or not so optimized, in the case of conveying pollen by blowing "in the open air" from the donor plant to the recipient plant, i.e. with no duct or channel for transporting the pollen between the donor and recipient plants.

Figure 2:
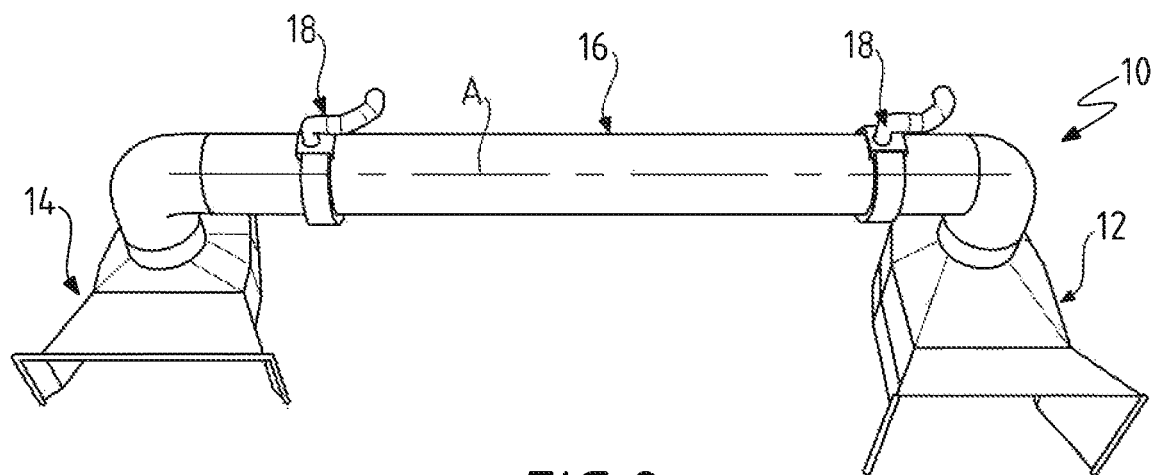
FIG. 2 represents a perspective view of another embodiment of an air-moving device.

As can be seen in FIG. 2, the conveying channel 16 may feature two elbows and a rectilinear portion between those two elbows. In this case, the conveying channel 16 extends in a rectilinear manner over at least 70%, preferably over at least 80%, more preferably over at least 90% of its total length. By extends in a rectilinear manner is meant that one or more portions of the conveying channel 16 extend(s) along one or more rectilinear axes. By way of example and with reference to FIG. 7, the conveying channel 16 may comprise a first portion 50 extending along a first portion of the conveying axis A and a second portion 52 extending along a second portion of the conveying axis A transverse to the first portion. This bidirectional extension of the conveying channel 16 therefore enables the collecting means 12 and the distributing means 14 to be disposed at different heights relative to the ground.

The conveying channel 16 may be adjustable along the conveying axis A to vary the distance between the collecting means 12 and the distributing means 14. To this end, the conveying channel 16 may be formed of telescopic ducts mounted one inside the other. The air-moving device 10 can therefore be adapted to different plant installation configurations. In fact, the donor plants may be separated from the recipient plants by distances varying according to the planting. Moreover, there may be different offsets between the passage of the supporting vehicle and the zones to be treated. The conveying channel 16 is preferably formed by at least one fixed duct and where applicable a duct mobile in translation. The fixed duct is preferably the duct on which a Coanda effect air flow amplifier 18 is mounted. When the mobile duct is disposed downstream of the fixed duct relative to the direction of the flow inside the conveying channel 16 the mobile duct is preferably mounted externally of the fixed duct so as to not to form an obstacle inside the conveying channel 16. The mobile duct then has a section greater than that of the fixed duct in this case of a downstream disposition. This makes it possible to limit the zones in which pollen may stick and to favor an increase of section in the final part of the conveying channel 16. Increasing the final section of the conveying channel 16 contributes effectively to reducing the speed of the pollen immediately before it arrives in the distributing means and therefore its deposition onto the recipient plants. Conversely, if the mobile duct is disposed upstream of the fixed duct relative to the direction of flow inside the conveying channel 16 the mobile duct is preferably mounted inside the fixed duct so as to not to form an obstacle inside the conveying channel 16. The mobile duct then has a section less than that of the fixed duct in this case of an upstream disposition.

To enable collection of the pollen present on the donor plant and transportation of that pollen to the distributing means 14, the air-moving device 10 also comprises a Coanda effect air flow amplifier 18 to induce a flow of air inside the conveying channel 16 from the pollen collecting means 12 to the pollen distributing means 14. This air flow amplifier 18 is configured to generate a Coanda effect enabling amplification of the flow of air inside the conveying channel 16. The air flow amplifier 18 enables induction upstream of the air flow amplifier of an aspiration air stream and downstream thereof of a blowing flow combining primary drive air injected into the conveying channel 16 and the induced secondary flow of air. The air flow amplifier 18 is preferably disposed at the level of the collecting means 12. In order to optimize the pollen aspiration air speeds, the air flow amplifier 18 is placed as close as possible to the point at which the pollen is aspirated, i.e. the collecting means 12. In fact, it is a question of inducing a minimum head loss in the conveying channel 16 in which the pressure is reduced upstream of the air flow amplifier 18 and the flow rate of which is less than the flow rate of the blowing flow downstream of the air flow amplifier 18. Thus most of the travel of the pollen in the conveying channel 16 is effected at positive pressure between the air flow amplifier 18 and the point of application, i.e. the distributing means 14. The head losses are then less harmful because they apply to a flow of air under pressure at a higher flow rate combining the primary drive air flow and the secondary air flow. Moreover, positioning the air flow amplifier 18 as far upstream as possible enables through the effect of the downstream head losses a reduction of the speed of the pollen before application thereof to the recipient plant. In particular, the air flow amplifier 18 is preferably disposed at the level of the first half of the conveying channel 16 following on from the collecting means 12. The air flow amplifier 18 is more preferably disposed at the level of the first third of the conveying channel 16 after the collecting means 12. The air flow amplifier 18, the drive air flow and the conveying channel 16 are configured so that the speed at which the pollen is transported inside the conveying channel 16 is less than 10 m·s$^{-1}$, preferably less than 5 m·s$^{-1}$, to limit the kinetic energy of the pollen, which is a function of the square of the speed of the latter, and thus to reduce as much as possible impacts and friction compromising the viability of the pollen. The speed at which the pollen is transported is nevertheless configured so as not to decrease to the point of causing pollen to settle on the walls of the conveying channel 16. It has been found that the limit pollen settling speed was around 0.10 to 0.20 m·s$^{-1}$. The air flow amplifier 18 and the conveying channel 16 are then also configured so that the speed at which the pollen is transported is above a speed range of 0.10 to 0.20 m·s$^{-1}$ to prevent the pollen from settling. The speed at which the pollen is transported is therefore preferably between 0.10 m·s$^{-1}$ and 10 m·s$^{-1}$ inclusive, more preferably between 0.10 m·s$^{-1}$ and 5 m·s$^{-1}$ inclusive. More generally, the conveying speed is adjustable and optimized as a function of the inherent settling rate of the transported pollen to prevent the pollen from being deposited on the walls of the conveying channel 16. The speed at which the pollen is transported inside the conveying channel 16 is therefore defined as a function of the inherent settling rate of each species of pollen transported. In particular, this speed at which the pollen is transported is defined as being greater than that inherent settling rate, or settling speed. The optimum conveying speed is more preferably that which prevents deposition of the pollen in the pipes whilst respecting its viability, seeking a minimum operational speed in order to make the transport of the pollen safe.

Moreover, to limit obstacles inside the conveying channel 16 the latter may have a pollen passage section in which the variation of section between the collecting means 12 and the distributing means 14 is less than or equal to 30%, preferably less than or equal to 20%, more preferably less than equal to 10%. The conveying channel 16 may have an increased pollen passage section downstream of the air flow amplifier 18 and in the vicinity of the distributing means 14 to enable the pollen to be slowed down before arrival thereof on the recipient plants and thus to favor the deposition thereof. This increase in the passage section of the conveying channel 16 is advantageously less than 30%, preferably less than 20%, more preferably less than 10% between the smallest passage section and the largest passage section of the conveying channel 16. The conveying channel 16 preferably includes no bifurcation or division from the conveying channel 16 to more than one distributing means 14. The conveying channel 16 therefore forms a continuous channel with no obstacles from the collecting means 12 to the distributing means 14.

As can be seen in FIG. 2, the air-moving device 10 may include a plurality of Coanda effect air flow amplifiers 18 disposed in series along the conveying channel 16 for each to participate in part in the induction of the secondary flow of air into the conveying channel 16. The air flow amplifiers 18 are disposed along the conveying channel 16 to enable amplification of the flow of air all along the conveying channel 16. It is therefore possible to maintain the pollen in suspension in order to prevent it from settling on the bottom of the conveying channel 16. Each apparatus creates upstream of its position a reduced pressure and downstream of its position a pressure enabling induction and movement of the flow of air. The action of the air flow amplifiers placed in series enables compensation over a longer pollen conveying distance of the head losses inherent to the circulation of the fluids in the pipes. The multiplication of the number of air flow amplification points also enables multiplication and lengthening in total of the zones having the benefit of the laminar flow primary drive air flow resulting from the Coanda effect that prevent the particles reaching the walls and settling there. The number of Coanda effect air flow amplifiers 18 placed in series is chosen as a function of the length of the conveying channel 16.

Figure 3:
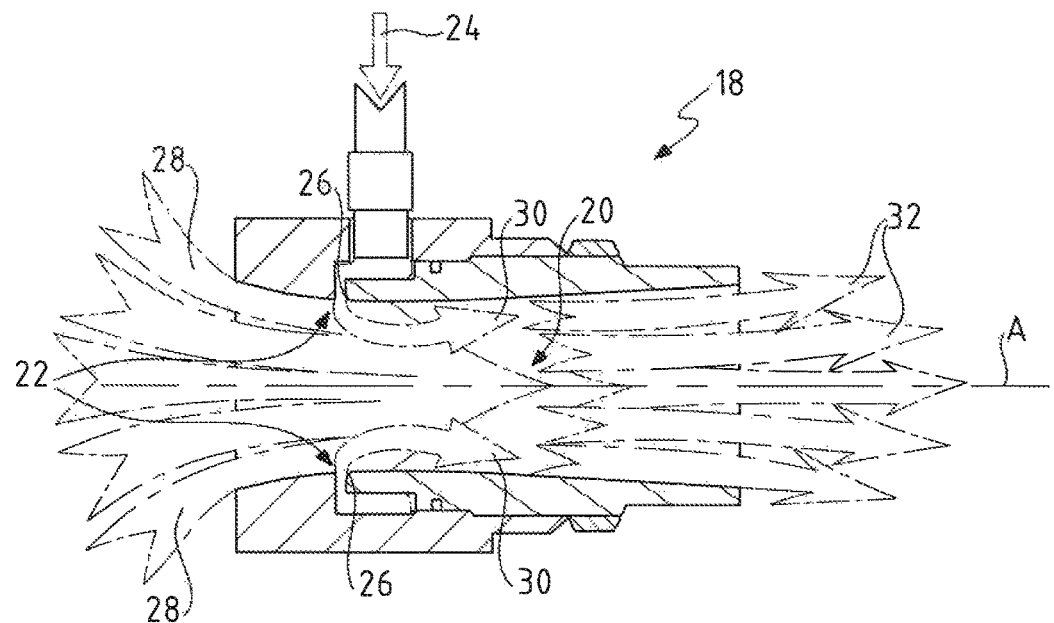
FIG. 3 represents a sectional view of a Coanda effect air flow amplifier.

As represented in FIG. 3, the Coanda effect air flow amplifier 18 preferably includes a pipe 20 forming a pipe element of the conveying channel 16 and an orifice 22 formed in the pipe 20. This pipe 20 preferably has a circular internal section for circulation of the flow of air free of any obstacle liable to induce undesirable contact with the pollen. The air flow amplifier 18 further comprises a source 24 of compressed gas in fluid communication with the orifice 22 to supply the conveying channel 16 with compressed gas. The source 24 preferably supplies the conveying channel 16 with compressed air taken from outside the conveying channel 16.

The source 24 is configured to inject the compressed air or the gas at low pressure, preferably at a pressure less than 0.1 MPa (1 bar). For the pollen of small grain cereals, the pressure inside the conveying channel is preferably less than 0.04 MPa (0.4 bar). The source 24 is preferably configured to supply air free of pollutants such as aerosols like condensed water or lubricants. Moreover, the source 24 may be configured to supply the gas or the air at a temperature substantially equal to the ambient temperature in order not to induce any significant change in the temperature of the pollen or intensifying modification of the hydrated state of said pollen. The source 24 is therefore preferably configured to supply the compressed air or the gas at a temperature between 15 and 25° C. The source 24 may be an unlubricated low-pressure compressor driven mechanically by the carrier vehicle and may equally be an air compressor turbine associated with a variable reluctance electric motor such as an internal combustion engine supercharger air compressor. Alternatively, the source 24 may comprise a centrifugal compressor associated with a brushless motor. In all these cases the source 24 preferably also includes a collar that may be an air/air exchanger to regulate the temperature of the compressed air or of the gas injected and to reduce its temperature to the ambient temperature. Moreover, the source 24 may comprise a device for draining any condensates, installed downstream of the cooling unit. These examples of the source 24 enable the conveying channel 16 to be supplied with very clean air.

The orifice 22 preferably extends along an angular sector around a conveying axis A along which the conveying channel 16 extends. The orifice 22 is more preferably circular and forms an annular orifice that extends around the conveying axis A. The drive air is therefore injected via the orifice 22 in the form of an annular air knife around the conveying axis A, at the periphery of the conveying channel 16. The section of the orifice 22 may be constant over all its circumference to induce an identical flow of air over all the perimeter of the air flow amplifier 18 and therefore in the portion of the conveying channel 16 downstream of the air flow amplifier 18. In other words, the section of the orifice 22 may be symmetrical about the conveying axis 16. Alternatively, the section of the orifice 22 may vary around the conveying axis 16 to induce a secondary flow of air having a speed varying around the conveying axis A. In other words, the section of the orifice 22 may be asymmetrical. This variation of the speed of the secondary flow of air is particularly advantageous for limiting the natural propensity of pollen to settle because of the effect of gravity and therefore to improve the retention of the pollen in suspension. To this end, the section of the orifice 22 is preferably greater in its upper part than in its lower part. In other words, the orifice 22 includes an upper portion having a section greater than the section of a lower portion disposed opposite the upper portion. This varying configuration of the section of the orifice 22 enables a greater pressure reduction to be induced at the level of the upper portion. If the air-moving device 10 comprises a plurality of air flow amplifiers 18, the latter may have a constant or varying section of the orifice 22. The section of the orifice 22 is preferably less than 1 mm, more preferably less than 0.5 mm. The orifice 22 may take the form of a calibrated slot.

The air flow amplifier 18 also has an interior edge 26 at least partly defining the orifice 22 and forming a convex surface the curvature of which is configured to generate a Coanda effect on a flow of compressed gas generated by the source 24 of compressed gas via the orifice 22. The edge 26 thus has a profile enabling generation of a Coanda effect. In particular, the profile of the edge 26 is configured to generate a Coanda effect where the amplification ratio between the secondary flow of air generated by the injection of the flow of primary drive air by the orifice 22 and the flow of primary drive air itself is at least equal to 10 and preferably greater than 15 and more preferably greater than or equal to 17. The edge 26 is disposed downstream of and in contact with the orifice 22 relative to the direction of movement of the flow of air in the conveying channel 16. The profile of the edge 26 may be produced by a curved surface. Alternatively, the convex profile of the edge 26 may be produced by a plurality of rectilinear segments to facilitate its manufacture.

Seen in cross section, the profile of the edge 26 preferably corresponds to a portion of an "NACA" profile as used in aeronautical construction, in particular the upper half of the "NACA" profile. The profile of the edge 26 therefore preferably comprises a leading edge disposed at the level of the orifice 22, a convex side and a trailing edge downstream of the air flow amplifier 18. For example, the profile of the edge 26 may correspond to an upper half of an "NACA0030" profile comprising a zero degree curvature of the reference line (from the leading edge to the trailing edge), a camber position of 0% and a profile thickness of 30% of the chord, i.e. the distance between the leading edge and the trailing edge.

The Coanda effect is the property of a flow of gas or liquid to follow an adjacent curved contour like the edge 26 without becoming detached therefrom. In a Coanda effect air flow amplifier the flow of primary drive air adheres to the curved surface in the form of a thin layer of high-velocity air that is accompanied by a zone of reduced pressure thereby inducing driving of the ambient air at a very high rate. The edge 26 is configured in such a manner as to cause the Coanda effect to endure over the greatest possible length in order to maximize the total area of high-velocity primary flow of air with by way of corollary driving of secondary air at a very high rate that explains the flow amplifying character of this kind of device.

FIG. 3 represents the blowing flow 32 induced by the air flow amplifier 18, combining the flow 30 of primary drive air injected into the conveying channel 16 and the flow 28 of secondary air. The flow 30 of primary drive air is annular and disposed at the periphery of the conveying channel 16 relative to the conveying axis A, in contact with the walls of the pipe 20. The aspiration flow 28 of secondary air is central relative to the conveying axis A and at a lower velocity than the flow 30 of primary drive air. For example, a flow 30 of primary drive air at a speed of 54 m·s$^{-1}$ at the level of the orifice 22 generates a flow 28 of secondary air at a velocity of 4 m·s$^{-1}$. To obtain a flow of secondary air at a speed of 10 m·s$^{-1}$, the drive air has at the level of the orifice 22 a speed of 86 m·s$^{-1}$. These examples of primary air flow 30 and secondary air flow 28 speeds are obtained for an annular orifice 22 having a diameter of 137 mm and a transverse dimension along the conveying axis A of approximately 0.3 mm in a Coanda effect flow amplifier with a nominal diameter of 200 mm. By the "nominal diameter" of the flow amplifier is meant the diameter of the ducts to which the flow amplifier is adapted to be connected. Thus a nominal diameter of 200 mm corresponds to a flow amplifier configured to be connected downstream and/or upstream of the flow amplifier to a duct having a diameter of 200 mm. This injection of an annular flow 30 of primary drive air therefore enables exposure of the aspirated pollen essentially upstream of the central zone of the flow 28 of secondary air at lower velocity.

The air flow amplifier 18 is configured to induce on the basis of the supply of compressed gas to the conveying channel 16 the flow 28 of secondary air at a predetermined speed where the ratio between said flow 28 of secondary air in the conveying channel 16 and the flow 30 of primary drive air is greater than or equal to 10, preferably greater than or equal to 15, more preferably greater than or equal to 17. In other words, the Coanda effect flow amplifier 16 enables generation of a flow 28 of secondary air from the flow 30 of primary drive air, the flow 28 of secondary air having a speed at least ten times less than the speed of the flow 30 of primary drive air at the level of the orifice 22. This amplification ratio is obtained in particular thanks to the profile of the edge 26. Accordingly, when the ratio between said flow 28 of secondary air in the conveying channel 16 and the flow 30 of primary drive air is equal to 17, the quantity 30 of inducing compressed gas is approximately equal to 6% of the downstream blowing flow 32. Coanda effect amplification therefore consumes little energy to obtain a blowing flow 32 at a predetermined speed, in particular in comparison to Venturi effect aspiration that generally enables only an amplification ratio of the order of 3 to be obtained. Coanda effect flow amplification therefore offers better performance, favors the generation of high flows at low pressure, and is generally used in systems aimed at finer flow optimization levels than systems using Venturi effect amplification that above all enable high aspiration and/or discharge pressures to be obtained.

The air flow amplifier 18 is preferably made of aluminum, the thermal conductivity of which enables prevention of cold spots generating condensation. The air flow amplifier 18 is preferably made from a material having a thermal conductivity greater than or equal to 150 W·m$^{-1}$·K−1. This condensation could soil the interior of the pollen conveying channel 16 and cause adhesion of pollen such that the reproductive potential of the pollen would be reduced. Cast aluminum is an example of a material suitable for the air flow amplifier 18.

The embodiment of the air flow amplifier 18 seen in FIG. 3 is for example supplied with the standardized dimension of approximately 200 mm (i.e. 8 inches). In this case the nominal diameter of the conveying channel 16 is preferably 200 mm to respect the preferred transport speeds.

Figure 4:
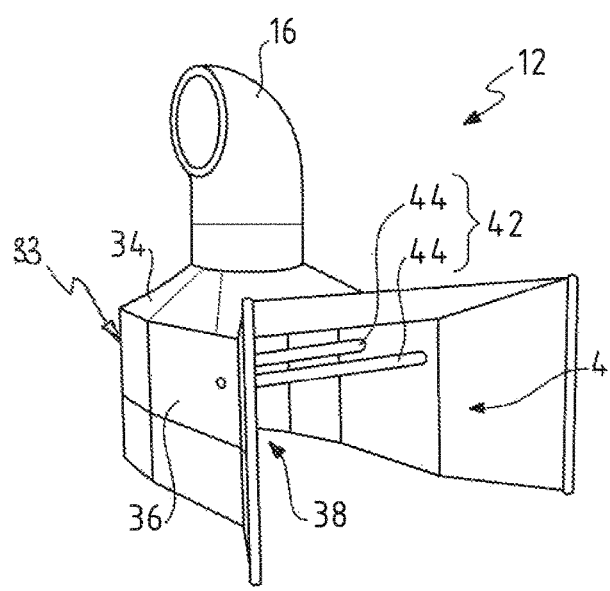
FIGS. 4 and 5 respectively represent a perspective view of a collecting means and of a distributing means of the air-moving devices represented in FIGS. 1 and 2.
Figure 5:
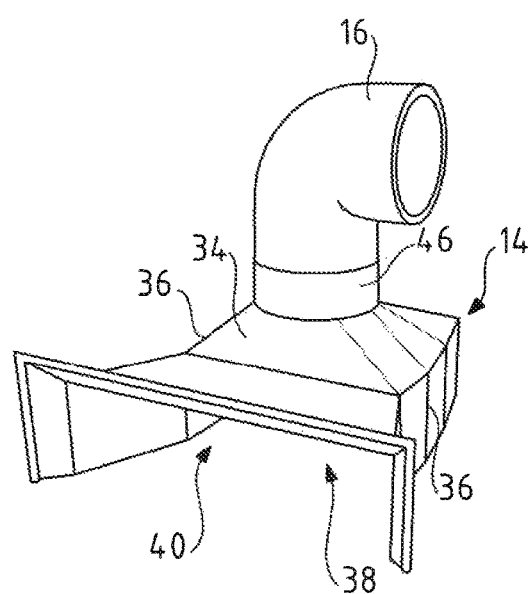

As represented in FIG. 4 the collecting means 12 is formed by a box 33 in which one or more donor plants is or are intended to be received. This box 33 comprises an upper wall 34 including an opening in fluid communication with the conveying channel 16 and two lateral walls 36 extending from the upper wall 34. In particular, the lateral walls extend transversely to the upper wall 34 to form a receiving cavity 38. The box 33 also comprises a front opening 40 enabling a donor plant to enter the box 33, in particular the receiving cavity 38.

The collecting means 12 also comprises a mobile back wall (not represented) disposed opposite the front opening 40 relative to the upper wall 34. The mobile back wall is configured to be moved in rotation by a donor plant. When the air-moving device 10 is moved in the direction of a donor plant, the latter therefore enters the collecting means 12 via the front opening 40, its pollen is collected, and then the advance of the air-moving device 10 leads to opening of the mobile back wall by the donor plant. The mobile back wall is for example fixed to the upper wall 34 by a hinge or a flexible material enabling the mobile back wall to be returned to its position closing the collecting means 12 by gravity or by a return force. The mobile back wall may also consist entirely of a flexible material, such as polyvinyl chloride. This mobile back wall makes it possible to orient the aspiration flow at the front of the collecting means 12. The lateral walls 36 are preferably conformed so that the distance separating the lateral walls 32 at the level of the front opening 40 is greater than the distance separating the lateral walls 36 at the level of the mobile back wall. The lateral walls 36 therefore form a truncated V or, in other words, a trapezoidal section. In other words, the lateral walls 36 converge toward the mobile back wall. This conformation enables concentration of the donor plants at the level of the opening in fluid communication with the conveying channel 16 so as to optimize the aspirated volume of air and consequently the speed at which the pollen is transported. For example, the distance separating the lateral walls 36 is 50 cm at the level of the front opening 40 and 30 cm at the level of the opening in fluid communication with the conveying channel 16. This reduced distance enables a 40% reduction of the volume of air necessary for effective transportation of the pollen. Moreover, the height of the lateral walls 36 and of the mobile back wall are chosen as a function of the height of the donor plants to be processed.

The collecting means 12 may also comprise deflector walls disposed around the front opening 40 to favor the entry of the donor plants into the collecting means 12.

Moreover, the collecting means 12 may comprise a shaking member 42 for shaking a donor plant disposed inside the box 33. The shaking member 42 comprises at least two rods 44 extending between the two lateral walls 36. Said at least two rods 44 are preferably spaced from one another in a first direction extending between the front opening 30 and the mobile back wall. Thus the rods 44 may be spaced from one another by 200 mm in the first direction. Moreover, the rods 44 may be spaced from one another in a second direction transverse to the first direction. Thus the rods 44 may be spaced from one another by 50 mm in the second direction. In other words, the rods 44 are spaced from one another in a substantially horizontal first direction and/or in a substantially vertical direction. The distance(s) separating the rods 44 in the first and/or the second direction may be adjustable to adapt to the type of donor plant or to the configuration of the terrain. The rods 44 are preferably mounted to rotate freely on themselves to limit rubbing on and injuring donor plants that are liable to be harvested more than once in the same season. The rods 44 may be coated with an adherent material in order to favor the rotation thereof on the passage of the donor plants.

In use, the first rod 44 disposed nearest the front strikes and lays down the inflorescence of the donor plant toward the front and performs a first shaking the speed of which is induced by the movement of the air-moving device 10. When the inflorescence is released from this first rod 44, it then strikes the second rod 44. The energy of shaking on the second rod 44 then cumulates the energy resulting from the speed of movement of the air-moving device 10 with the escape energy acquired on retention under the first rod 44. The height difference between the two rods 44 enables the second shaking to be applied essentially at the level of the inflorescence in order to induce a plurality of to and fro movements of the inflorescence to extract therefrom the pollen contained in its anthers.

For example, in a configuration for small grain cereals, the receiving cavity 38 advantageously has a width of 300 mm and a depth of 300 mm so that the mean aspiration air speed is approximately 1.4 $m \cdot s^{-1}$ at the level of the opening in fluid communication with the conveying channel 16. This aspiration air speed makes it possible to combat the natural falling of pollen inside the collecting means 12 and to induce rising thereof in the conveying channel 16. If the air-moving device 10 is moved at a speed of advance of 2 $km \cdot h^{-1}$, an ear of the donor plant remains on average 0.25 s under the opening in fluid communication with the conveying channel 16. During this resting time of 0.25 s the mean aspiration air flow rises approximately 0.35 m, enabling the pollen to be engaged in the upward major aspiration flow having a speed of 4 $m \cdot s^{-1}$ present in the conveying channel 16, from which conveying channel the pollen is unable to redescend. An ear remains in the operational plane for longer under the aspiration flow that commences at the very mouth of the collecting means 12 and is extended to the rear of the conveying channel 16 over a total length of 700 mm, i.e. a potential duration of approximately 0.7 s. This aspiration time increases the overall effectiveness of the pollen collecting means 12 and contributes to optimizing the volume 28 of aspiration air.

As represented in FIG. 5, the distributing means 14 is also formed by a box 33 in which one or more recipient plants are intended to be received. The distributing means 14 is similar to the collecting means 12 except that the box 33 does not comprise any back wall in order not to impede the distribution of the pollen onto the recipient plant or plants and to induce an undesirable final shaking. The distributing means 14 adopts the same trapezoidal box general shape as the collecting means 12 in order to concentrate the recipient plants under the blowing flow laden with pollen coming from the conveying channel 16. In the embodiment for small grain cereals, grouping the recipient plants under the pollination flow enables a 66% increase in the target surface area to be pollinated and thus to limit losses of pollen. Moreover, the box 33 of the distributing means 14 comprises no shaking member 42. The box 33 of the distributing means 14 therefore comprises two lateral walls 36 and an upper wall 34 in which is formed an opening in fluid communication with the conveying channel 16. The height of the lateral walls is chosen as a function of the height of the inflorescences of the recipient plants to be processed. Moreover, elements for adjusting the height of the collecting means 12 and the distributing means 14 may be added in order to adapt them to the pollen donor and recipient varieties, which are generally of different heights. These elements for adjusting the height may take the form of duct portions added between the end of the conveying channel 16 and the collecting means 12 or, where appropriate, between the end of the conveying channel 16 and the distributing means 14.

The distributing means 14 may also be preceded by a section of the conveying channel 16 consisting of a material 46 generating triboelectric charges 46 disposed in the passage for the transported pollen. This section of the conveying channel 16 is preferably disposed in the vicinity of the distributing means 14. In fact, the natural pollination of anemogamous plants pollinated by the action of the wind such as poaceae (wheat, barley, rice, maize, etc.) is in part accomplished thanks to the action of electrostatic charges acquired by the grains of pollen that optimize the capture of the pollen by the female members. For example, the triboelectric charge generator 46 may be a duct portion comprising a material generating induced triboelectric charges by rubbing of the air transporting the pollen on the walls. To optimize this phenomenon, the duct portion is preferably disposed at the end of the conveying channel 16 to transmit these triboelectric charges just before the distribution of the pollen onto the recipient plants.

Alternatively, the distributing means 14 may have no box 33. In this case the distributing means 14 may be one end of a conveying channel 16 oriented toward a recipient plant. As a further alternative the lateral walls of the box 33 of the distributing means 14 may be replaced by convergent guides for grouping recipient plants under the pollination flow. These convergent guides form a preferably trapezoidal armature to cause the recipient plants to converge under the pollination flow. The use of convergent guides enables reduction of the mass of the distributing means 14 whilst producing the convergence of the recipient plants. This is particularly advantageous when it is required to increase the dimensions of the distributing means 14 to cause a greater number of recipient plants to converge under the pollination flux so as to optimize the density of potential targets.

The air-moving device 10 may also be associated with one or more other air-moving devices 10 to form an air-moving apparatus for pollinating at least one recipient plant using pollen collected from at least one donor plant. Each air-moving device 10 therefore forms an independent pollination module. This modular design of the air-moving device 10 enables a plurality of air-moving devices 10 to be combined to cover a larger area of donor plants as well as a larger area of recipient plants. FIG. 6 represents for example a vehicle 47 comprising a coupling structure 48 and an air-moving apparatus 54 disposed on the coupling structure 48. Here the air-moving apparatus comprises three air-moving devices 10 disposed side by side so that the conveying channels 16 of the air-moving devices 10 extend in the same direction. Each of the air-moving devices is offset relative to the others in that direction to enable the successive disposition of the collecting means 12 and the distributing means 14 of each of the air-moving devices 10. In particular, the air-moving devices 10 are disposed so that each of the front openings 40 of the collecting means 12 and the distributing means 14 of the air-moving devices 10 are oriented in the same direction of advance to receive donor or recipient plants during movement of the vehicle 47 in that direction of advance.

The vehicle 47 may also include an independent module 56 for evaluation of the quantitative potential of pollen used during pollination. A very minor portion of the pollen resource may therefore be intended for measuring the pollen potentially available for pollination. The pollen collected in this independent evaluation module 56 is representative of the quantity of pollen aspirated and applied by each of the air-moving devices. This independent evaluation module 56 comprises a collecting means 12 similar to that of the air-moving devices 10, a conveying channel 16 and a Coanda effect air flow amplifier 18. Here this air flow amplifier 18 is used only to aspirate the pollen and to move it as far as a separation cyclone. It may be replaced with a simple fan because the pollen, previously returned in the separation cyclone, does not come into contact with the means for generating the flow of aspiration air placed at the outlet of the cyclone. The pollen is then recovered in a reservoir to be able to quantify the mass or the number of grains of pollen aspirated per unit surface area.

Figure 6:
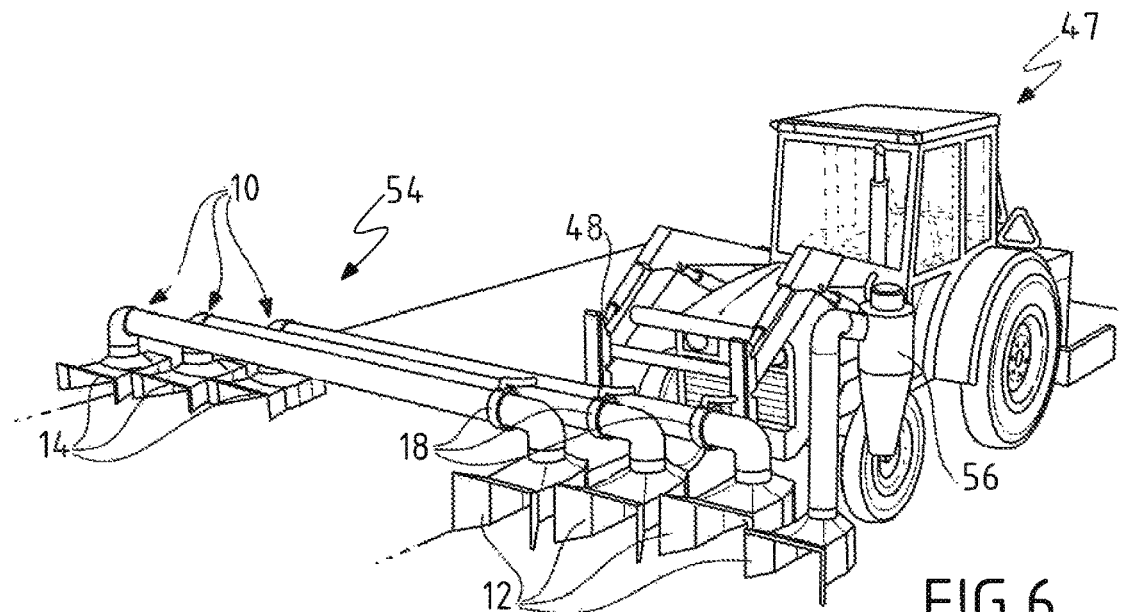
FIG. 6 represents a perspective view of one embodiment of a vehicle comprising a coupling structure and a plurality of air-moving devices as represented in FIG. 2.

Respecting the reproduction potential of the pollen has been the subject of comparative measurements of the viability of the pollen before and after passage in the air-moving device 10 as represented in FIG. 6. Those evaluations have demonstrated the innocuous nature of this pollination technology on the reproductive potential of the pollen. To this end, a flow cytometry technology specifically dedicated to evaluating the reproductive potential of the pollen has been used. That technology has been developed and marketed by the company Amphasys AG.

Figure 7:
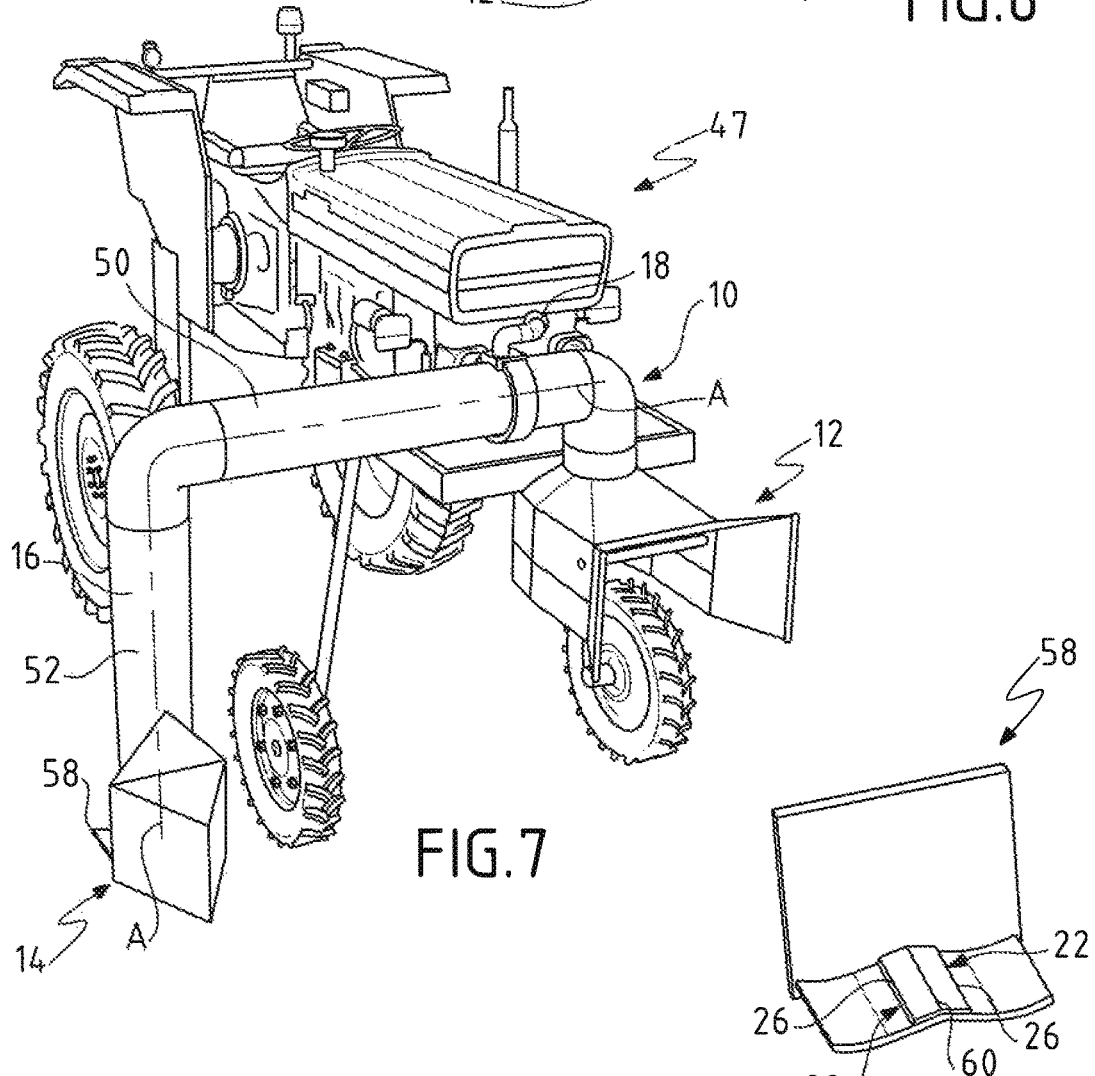
FIG. 7 represents a perspective view of another embodiment of a vehicle having a configuration suitable for tall plants.

As represented in FIG. 7, the vehicle 47 may be configured for plants of great height, such as maize or other tall root crop plants. A specific configuration of the vehicle 47 is preferable for tall plants. In fact, these plants have a great height but above all may include flowers that are not hermaphroditic, which implies that the donor and recipient zones of these plants are located at different heights on the plant. This implies different pollen collection and application points able to vary in space independently of one another.

In this embodiment for tall plants the vehicle 47 comprises an air-moving device 10 specifically configured for plants of great height. In this case the air-moving device 10 features in particular an important height difference between the collecting means 12 and the distributing means 14. To this end, the conveying channel 16 comprises a first portion 50 extending along a first portion of the conveying axis A and a second portion 52 extending along a second portion of the conveying axis B transverse to the first portion. This bidirectional extension of the conveying channel 16 enables the collecting means 12 and the distributing means 14 to be disposed at different heights relative to the ground whilst minimizing obstacles inside the conveying channel 16. Replacing this L shape of the conveying channel with a curved duct portion the curvature of which is continuous from the collecting means 12 to the distributing means 14 as represented in FIG. 1 may also be envisaged.

Figure 8:
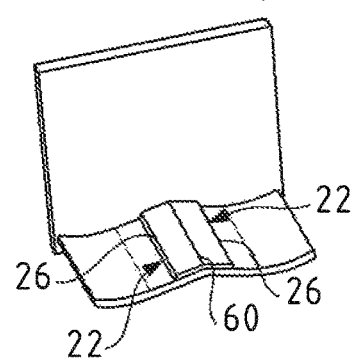
FIG. 8 represents a perspective detail view of a pneumatic deflector of an air-moving device as represented in FIG. 7.

As represented in FIG. 8, there is also proposed a Coanda effect pneumatic pollen deflector 58 disposed at the level of the distributing means 14 to induce a flow of air transverse or more generally orientable relative to the conveying axis A of the second portion 52 of the conveying channel 16. This flow of air constitutes a pneumatic deflector and enables prevention of all contact between the pollen and physical deflector wall. The pollen is therefore distributed on one or more axes at speeds controlled by the supply air pressure of the pneumatic deflector 58. The pneumatic deflector 58 employs the same mode of operation as the air flow amplifier 18. To this end, the pneumatic deflector 58 includes for each of these deflection axes an orifice 22 produced in a distributor 60 and delimited by an edge 26 forming a convex surface configured to generate a Coanda effect generating a thin layer of fluid at high velocity and air flow amplification. When the Coanda effect deflector distributes the pollen flow along a plurality of deflection axes it also serves the purpose of dividing the pollen flow routed in the pipe 16. Dividing the main pollen flow routed via the pipe 16 into a plurality of secondary flows may be effected in cascade by a succession of Coanda effect deflectors 58. A source 24 enables supply of compressed gas to the orifice 22. In particular, the pneumatic deflector 58 with two deflection axes represented by way of example in FIG. 8 comprises two orifices 22 extending in a rectilinear manner transversely to the flow of blowing air coming from the conveying channel 16. A flow of air for deflecting the pollen is therefore generated by the pneumatic deflector 58 to orient the flow of blowing air coming from the conveying channel 16 and consequently the pollen in a predetermined direction. This selective orientation ahead of any contact between the pollen and a physical wall enables prevention of all impact or rubbing lethal to the pollen before being distributed to the recipient plants.

Figure 9:
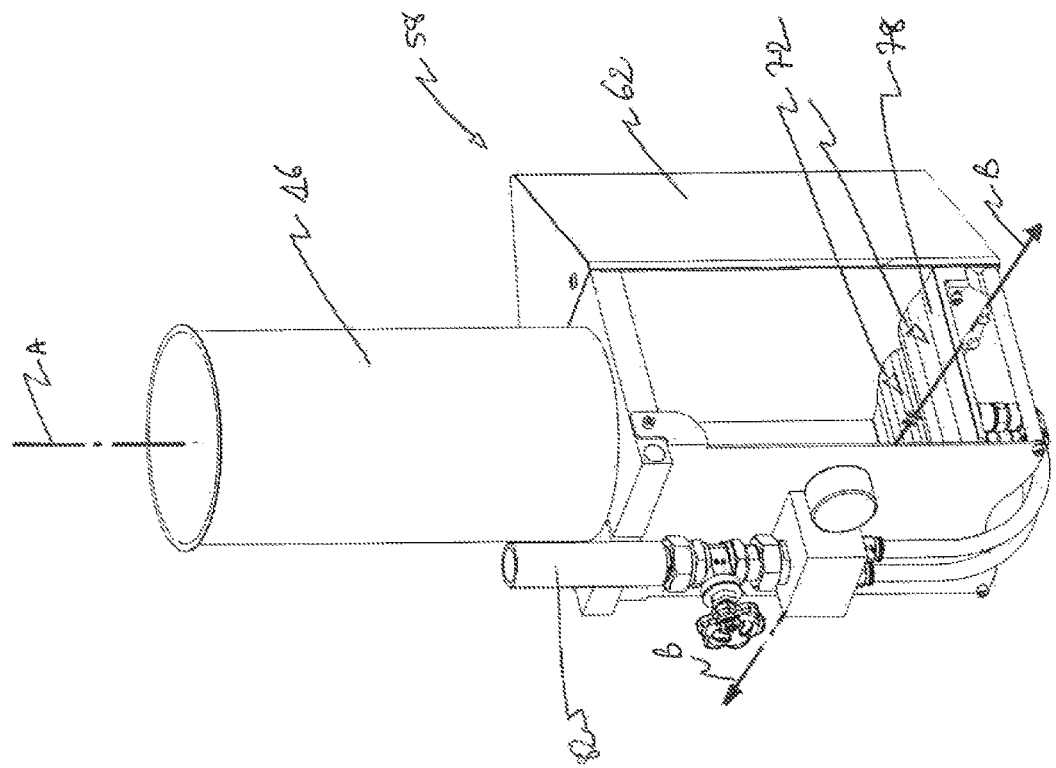
FIGS. 9 and 10 represent a perspective view and a sectional view of one embodiment of the pneumatic deflector.
Figure 10:
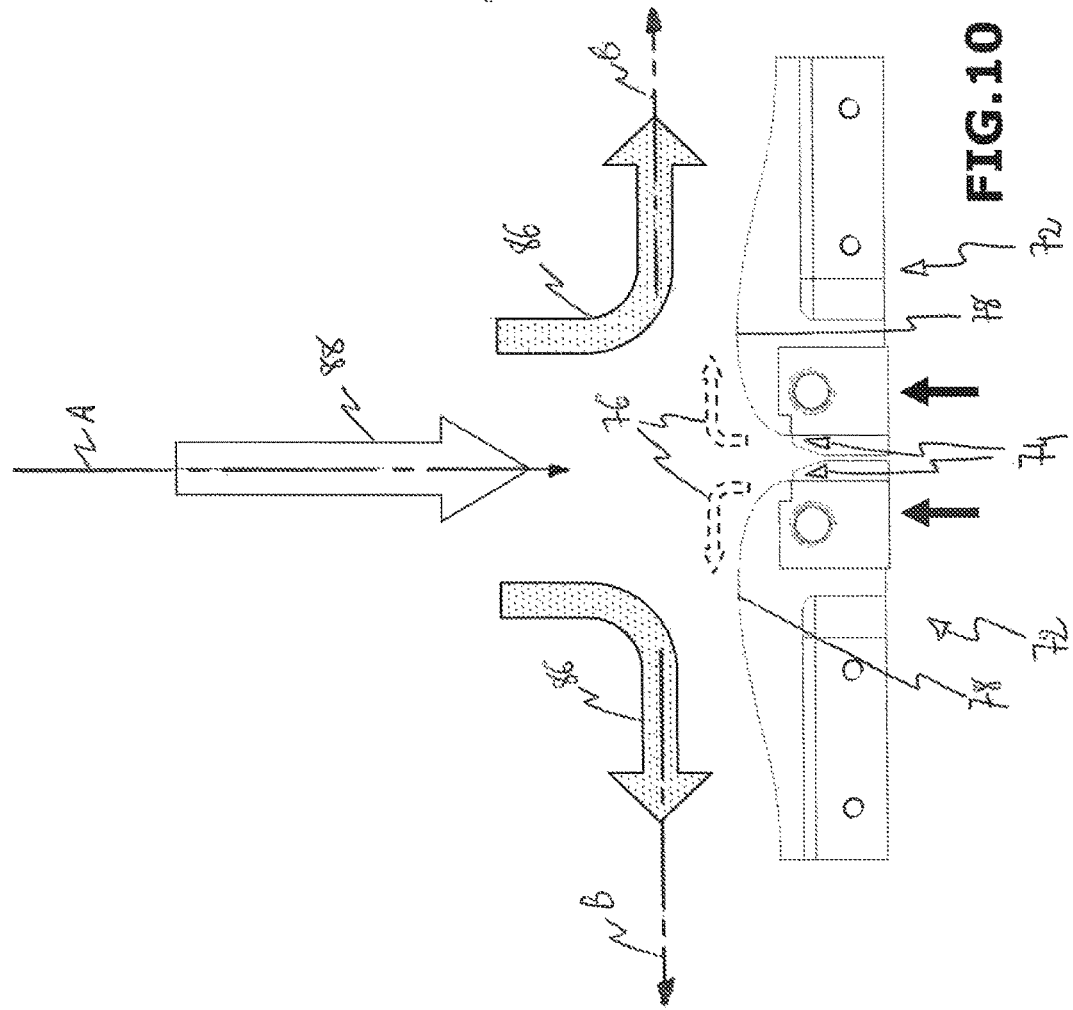

An embodiment of a Coanda effect biaxial pneumatic pollen deflector 58 is also represented in FIGS. 9 and 10. By "biaxial" is meant that the pneumatic deflector 58 is configured to induce a flow of air for deflecting the pollen along two deflection axes B.

In this embodiment the pneumatic deflector 58 is connected directly to the end of the conveying pipe 16. Thus here the distributing means 14 corresponds to the outlet orifice formed by the conveying pipe 16.

The deflection axes B are preferably transverse to the conveying axis A along which the pollen circulates to the outlet of the conveying pipe 16. The pollen is therefore preferably redirected toward the sides of the pneumatic deflector 58 relative to the direction of movement of the air-moving device 10. The pneumatic deflector 58 preferably comprises a front shield 62 configured to guide the recipient plants toward at least one side of the pneumatic deflector 58. The recipient plants are therefore guided toward a lateral zone of the pneumatic deflector 58 where the pollen is redirected by the pneumatic deflector 58.

The pneumatic deflector 58 comprises one or more Coanda effect deflecting means 72 each configured to generate a thin layer of fluid at high velocity and air flow amplification by the Coanda effect to divert the flow of pollen along a deflection axis B. Each deflection means 72 forms an orifice 74 for injection of a primary or drive air flow 76 and a profile 78 configured to optimize the Coanda effect on the flow 76 of primary gas. The profile 78 defines at least in part the orifice 74 and forms a convex surface the curvature of which is configured to generate a Coanda effect on the flow 76 of compressed gas generated by a source of compressed gas via the orifice 74. The profile 78 more particularly forms a convex surface configured to generate a Coanda effect to generate a thin layer of fluid at high velocity and air flow amplification to induce a deflector flow of air along one or more of the deflection axes B. The profile 78 thus constitutes a surface enabling generation of a Coanda effect. The profile 78 forms a surface oriented in such a manner as to face the flow 88 of pollen coming from the conveying pipe 16. The profile 78 is disposed downstream of contact with the orifice 74 relative to the direction of movement of the flow 76 of primary air. The profile 78 may be produced by a curved surface. Alternatively, the convex profile of the edge 78 may be produced by a plurality of rectilinear segments to facilitate its manufacture.

When the pneumatic deflector 58 comprises a plurality of Coanda effect deflection means 72 enabling diversion of the pollen flow along a plurality of deflection axes B, the pneumatic deflector 58 can make it possible to divide the pollen flow. By way of example, the configuration of the pneumatic deflector 58 represented in FIGS. 9 and 10 enables division of the pollen flow 88 into two diverted pollen flows 86. The position of the deflector members 72 relative to the conveying axis A enables regulation of the proportion of each of these diverted pollen flows 86.

As represented in FIG. 10, when seen in cross section the profile 78 preferably corresponds to a portion of an "NACA" profile used in aeronautical construction, in particular the upper half of the "NACA" profile. The profile 78 therefore preferably comprises a leading edge disposed at the level of the orifice 74, a convex surface and a trailing edge downstream of the deflector means 72. By way of example, part of the profile 78 may correspond to an upper half of an "NACA0030" profile comprising a zero degree camber of the reference line (from the leading edge to the trailing edge), a camber position of 0% and a profile thickness of 30% of the chord, i.e. the distance between the leading edge and the trailing edge.

Figure 11:
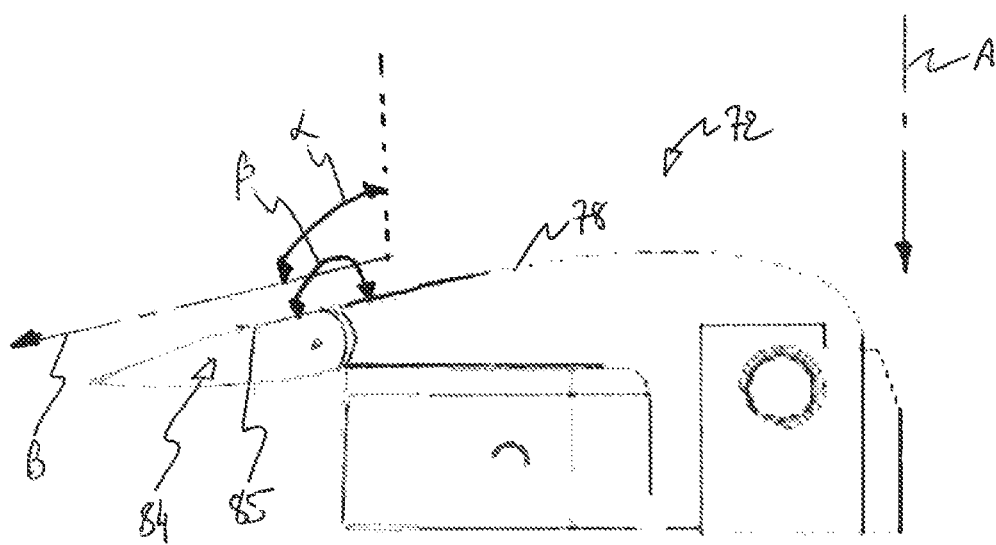
FIGS. 11 to 13 represent sectional views of one embodiment of the pneumatic deflector comprising a mobile flap.
Figure 12:
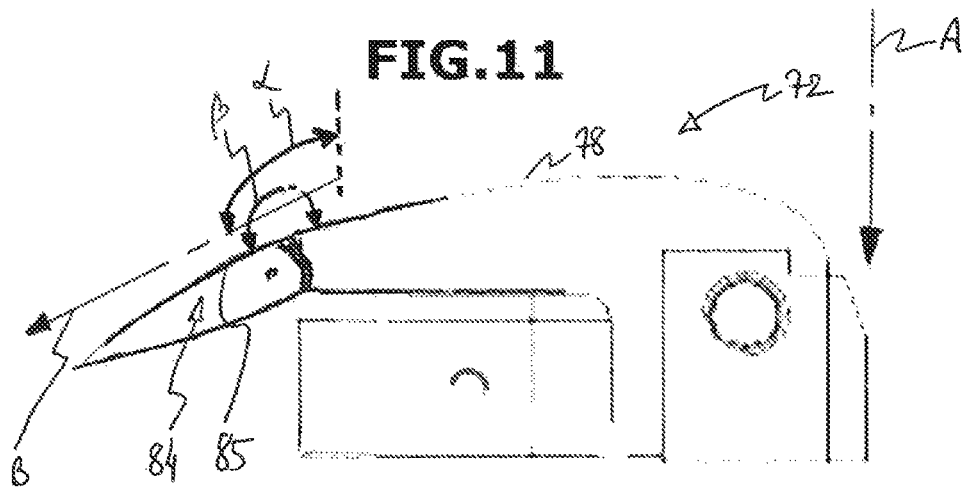
Figure 13:
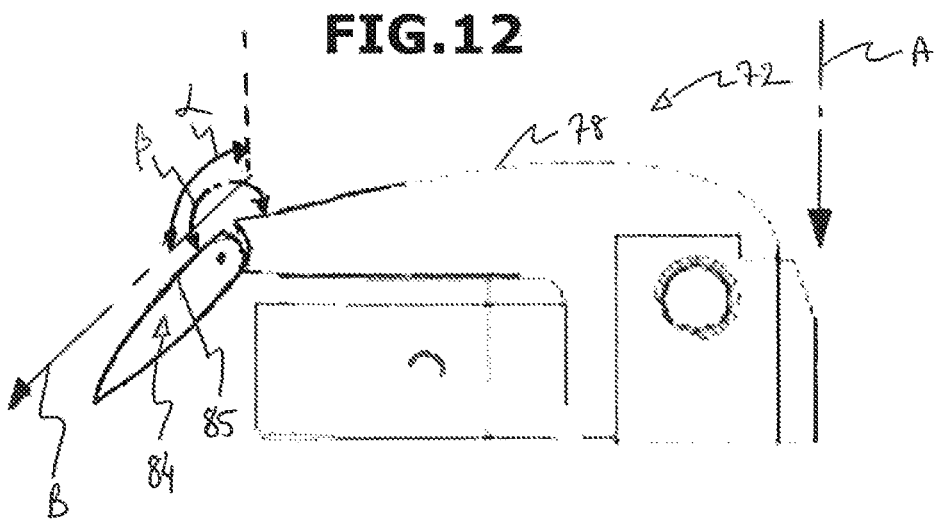

As shown in FIGS. 11-13, the deflector means 72 may also comprise a mobile part at the level of an end 80 of the profile 78 opposite the orifice 74. The mobile part preferably forms a trailing edge of the profile 78. In other words, the deflector member 72 may comprise a trailing edge mobile in rotation about an axis extending transversely to the deflection axis B. This mobile part is preferably a mobile flap 84, known as a curvature flap in the aeronautical field, enabling the overall curvature of the profile 78 to be changed so as to increase the possibilities of adjusting a deflection angle α of the pollen flow. The deflection angle α of the pollen flow is preferably defined as the angle between the conveying axis A and the deflection axis B in a plane transverse to the profile 78. The mobile part, or the mobile flap 84, is configured to cause the deflection angle α to vary as a function of the inclination of the mobile flap 84 about its rotation axis. The inclination of the mobile flap 84 also defines a curvature angle β between the surface of the profile 78 and an upper surface 85 of the mobile flap 84 in a plane transverse to the profile 78. As represented in FIG. 13, for a curvature angle β greater than a predetermined angle, for example greater than 210°, the mobile flap 84 also enables separation of the laminar air streams circulating over the fixed part of the profile 78. The separation of the air streams from the profile 78 at the level of the mobile flap 84 induces turbulence favorable to slowing down and dispersing the grains of pollen before application thereof to the recipient plants.

FIG. 10 represents the flow 88 of pollen coming from the conveying pipe 16 diverted by the deflector means 72, combining the flow 76 of primary drive air injected and the diverted pollen flow 86. The pollen flow 88 coming from the conveying pipe 16 along the conveying axis A is therefore divided and redirected along the two deflection axes B by the deflector means 72.

The pneumatic deflector 58 further comprises a source of compressed gas in fluid communication with each orifice 74 of the deflector means 72 to supply it with compressed gas. In the case of a plurality of deflector members 72 producing multiaxial deflection, the pressure of the primary drive gas 76 from each deflector member 72 may be adjusted individually so as to produce a division and a deflection of the flow of pollen that can be asymmetrical. This compressed gas is preferably generated by the source using air collected from outside the environment of the pneumatic deflector 58.

The source is configured to inject the compressed air or the gas at low pressure, preferably at a pressure less than 0.1 MPa (1 bar). The source is preferably configured to supply air free of pollutants such as aerosols like condensed water or lubricants. Moreover, the source may be configured to supply the gas or the air at a temperature substantially equal to the ambient temperature in order to induce no significant change in the temperature of the pollen or to intensify modifications of the hydrated state of said pollen. The source is preferably configured to supply the compressed air or the gas at a temperature between 15 and 25° C. inclusive. The source may be an unlubricated low-pressure compressor driven mechanically by the support vehicle or another autonomous internal combustion engine; it may equally be an air compressor turbine associated with a variable reluctance electric motor such as an internal combustion engine supercharger air compressor. Alternatively, the source may comprise a centrifugal compressor associated with a brushless electric motor. In all these cases, the source preferably also comprises a cooling unit that may be an air/air exchanger to regulate the temperature of the compressed air or the gas injected and reduce its temperature to ambient temperature. Moreover, the source may comprise a device for draining any condensates, installed downstream of the cooling unit. These source examples enable the pneumatic deflector 58 to be supplied with very clean air. The source is preferably the source 24 of the pollen transfer air flow amplifier 18 so that the compressed gas supplying the orifice 74 also comes from the same source 24. This latter example corresponds in particular to the embodiment represented in FIG. 9 in which the compressed gas supplying the orifices 74 is injected by means of the duct 82.

The orifice 74 is preferably a slot extending along the upstream end of the profile 78. The slot may be rectilinear for example along the upstream edge of the profile 78. Thus the drive air is injected through the orifice 74 in the form of an air knife.

The orientation of each of the profiles 78 is preferably selectively variable in such a manner as to cause to vary the direction of one or more of the deflection axes B.

The profiles 78 are preferably made from a material having a thermal conductivity and a thermal inertia enabling the temperature at the surface of the profiles 78 not to fall below a predetermined threshold. That predetermined threshold is chosen to prevent all condensation on the surface of the profiles 78. Moreover, the thickness of the profiles 78 is chosen in such a manner as to increase the thermal conductivity and the thermal inertia of the profiles 78. The external surface of the profiles 78 is preferably produced by machining to obtain a more accurate profile enabling an optimized Coanda effect and improved deflection of the flow 86 of air. The profiles 78 are preferably made of aluminum to enable respect for thermal and surface state qualities.

Moreover, the pneumatic deflector 58 may comprise a means for varying the distance separating the end of the conveying pipe 16 from the profiles 78 that enables variation of the required deflection angle and force.

The invention claimed is:

1. An air-moving device for pollinating at least one recipient plant using pollen collected on at least one donor plant, comprising:

a collecting means for collecting pollen from said at least one donor plant, a distributing means for distributing pollen on at least one recipient plant, a conveying channel for conveying the pollen collected from the collecting means to the distributing means, an air flow amplifier, forming a part of said conveying channel which employs Coanda effect for inducing a flow of air inside the conveying channel from the means for collecting the pollen to the means for distributing the pollen, wherein the conveying channel has a pollen passage section, wherein variation of the pollen passage section between the collecting means and the distributing means is equal to or less than 30% of the pollen passage between a smallest passage section and a largest passage section of the conveying channel.

2. The device as claimed in claim 1, in which the conveying channel is formed by a plurality of pipe elements, the Coanda effect air flow amplifier including:

a pipe forming one of said pipe elements of the conveying channel, an orifice formed in the pipe, a source of compressed gas in fluid communication with the orifice to feed the conveying channel with compressed gas, an interior edge at least partly defining the orifice and forming a convex surface configured to generate a Coanda effect on a primary drive gas flow generated by the source of compressed gas via the orifice.

3. The air-moving device as claimed in claim 2, in which the conveying channel extends around a conveying axis, the orifice extending along an angular sector around the conveying axis.

4. The air-moving device as claimed in claim 2, in which the air flow amplifier is configured to induce on the basis of the supply of compressed gas to the conveying channel a secondary flow of air at a predetermined speed where the ratio between said secondary air flow in the conveying channel and the primary drive gas flow is greater than or equal to 10.

5. The air-moving device as claimed in claim 1, in which the Coanda effect air flow amplifier is disposed proximate to the collecting means.

6. The air-moving device as claimed in claim 1, comprising a plurality of Coanda effect air flow amplifiers disposed in series along the conveying channel to participate at least partly in inducing the secondary flow of air inside the conveying channel.

7. The air-moving device as claimed claim 1, in which the conveying channel extends in a rectilinear manner over at least 70% of the length of said conveying channel.

8. The air-moving device as claimed in claim 1, in which the conveying channel is formed by a pipe comprising at the maximum three elbow portions between the collecting means and the distributing means.

9. The air-moving device as claimed in claim 1, in which each of the collecting means and the distributing means is formed by a box comprising:

an upper wall having an opening in fluid communication with the conveying channel, two lateral walls extending from the upper wall, a front opening enabling the donor plant or the recipient plant to enter the box.

10. The air-moving device as claimed in claim 9, in which the collecting means further comprises:

a mobile back wall disposed opposite the front opening relative to the upper wall, and/or a shaking means for shaking a donor plant disposed inside the box.

11. The air-moving device as claimed in claim 10, in which the shaking means comprises at least two rods extending between the two lateral walls, said at least two rods being spaced from one another in a direction extending between the front opening and the back wall.

12. The air-moving device as claimed in claim 1, further comprising one or more pneumatic deflectors for deflecting the Coanda effect flow of pollen disposed at the level of the distributing means.

13. An air-moving device as claimed in claim 1 for a type of pollen having a predetermined settling rate, in which the Coanda effect air flow amplifier induces a flow of air inside the conveying channel at a speed greater than the predetermined settling rate.

14. The air moving device as claimed in claim 13, in which the speed of the flow of air induced inside the conveying channel is equal to or less than 10 $m \cdot s^{-1}$, preferably equal to or less than 5 $m \cdot s^{-1}$.

15. An air-moving apparatus for pollinating at least one recipient plant using pollen collected from at least one donor plant, comprising at least two air-moving devices as claimed in claim 1 disposed side by side so that the conveying channels of each of the air-moving devices extend in the same direction, one of the air-moving devices being offset relative to the other air-moving device in said direction.

16. A vehicle comprising a coupling structure and at least one device as claimed in claim 1, fixed to the coupling structure so that each of the front openings of the collecting means and the distributing means of the air-moving devices are oriented in the same direction of advance to receive donor plants or recipient plants during movement of the vehicle in that direction of advance.

* * * * *